United States Patent
Worst et al.

(10) Patent No.: US 7,179,292 B2
(45) Date of Patent: Feb. 20, 2007

(54) INTRAOCULAR LENS FOR IMPLANTATION IN AN EYE AND INSTRUMENT AND METHODS FOR INSERTION OF SUCH A LENS

(75) Inventors: Jan Gerben Frans Worst, Haren (NL); Harry Franciscus Simon, Groningen (NL); Martinus Aponno, Haren (NL)

(73) Assignee: Ophtec B.V. (NL)

( * ) Notice: Subject to any disclaimer, the term of this patent is extended or adjusted under 35 U.S.C. 154(b) by 23 days.

(21) Appl. No.: 10/389,514

(22) Filed: Mar. 14, 2003

(65) Prior Publication Data
US 2004/0015235 A1    Jan. 22, 2004

Related U.S. Application Data

(60) Provisional application No. 60/364,514, filed on Mar. 15, 2002.

(51) Int. Cl.
*A61F 2/14* (2006.01)

(52) U.S. Cl. ..................... 623/6.43; 623/6.47
(58) Field of Classification Search ............... 623/4.1, 623/6.11, 6.12, 6.18, 6.38, 6.39, 6.43, 6.46, 623/6.47
See application file for complete search history.

(56) References Cited

U.S. PATENT DOCUMENTS

| | | |
|---|---|---|
| 3,913,148 A | 10/1975 | Potthast |
| 4,122,556 A | 10/1978 | Poler |
| 4,143,427 A | 3/1979 | Anis |
| 4,530,117 A * | 7/1985 | Kelman ................. 623/6.12 |
| 4,560,383 A | 12/1985 | Leiske |
| 4,573,998 A | 3/1986 | Mazzocco |
| 4,726,367 A * | 2/1988 | Shoemaker ............ 606/107 |
| 4,863,464 A | 9/1989 | Dusek |
| 4,863,465 A | 9/1989 | Kelman |
| 4,878,910 A | 11/1989 | Koziol et al. |
| 4,880,426 A | 11/1989 | Ting et al. |
| 4,888,014 A | 12/1989 | Nguyen |
| 4,894,062 A | 1/1990 | Knight et al. |
| 4,917,680 A | 4/1990 | Poley |

(Continued)

FOREIGN PATENT DOCUMENTS

AU        200028115 B2    9/2000

(Continued)

*Primary Examiner*—Corrine McDermott
*Assistant Examiner*—William H Matthews
(74) *Attorney, Agent, or Firm*—Akerman Senterfitt

(57) ABSTRACT

An intraocular lens includes an optical portion (7; 607; 907; 1107) of a transparent, deformable material, at least one haptic (5, 6; 205, 206; 405, 406, 706; 806; 905; 1005; 1105; 1205) radially projecting from the optical portion for supporting the optical portion in a position parallel to and against an anterior iris surface plane (936; 1136), and at least one aperture (13; 213; 713; 913; 1013; 1113) bounded by the haptic. At least a stiff portion of the haptic has a higher stiffness against bending about an axis in the radial direction than the optical portion. Furthermore, the stiff portion has a width (a) measured parallel to the plane and perpendicular to the radial direction, which is smaller than the size (b) of the optical portion in the direction of the width. An instrument and methods for preparing and carrying out insertion of such a lens are also described.

9 Claims, 11 Drawing Sheets

U.S. PATENT DOCUMENTS

| | | |
|---|---|---|
| 4,919,662 A | 4/1990 | Knoll et al. |
| 4,961,745 A | 10/1990 | Graham et al. |
| 4,963,149 A | 10/1990 | Anis |
| 4,990,159 A | 2/1991 | Kraff |
| 5,013,322 A | 5/1991 | Rosa |
| 5,041,135 A | 8/1991 | Charleux |
| 5,047,051 A | 9/1991 | Cumming |
| 5,118,452 A | 6/1992 | Lindsey et al. |
| 5,147,395 A | 9/1992 | Willis |
| 5,171,268 A | 12/1992 | Ting et al. |
| 5,180,390 A | 1/1993 | Drews |
| 5,192,319 A | 3/1993 | Worst |
| 5,201,763 A | 4/1993 | Brady et al. |
| 5,203,790 A | 4/1993 | McDonald |
| 5,211,662 A | 5/1993 | Barrett et al. |
| 5,266,241 A | 11/1993 | Parekh |
| 5,290,892 A | 3/1994 | Namdaran et al. |
| 5,306,297 A | 4/1994 | Rheinish et al. |
| 5,322,649 A | 6/1994 | Rheinish et al. |
| 5,326,506 A | 7/1994 | Vanderbilt |
| 5,331,073 A | 7/1994 | Weinschenk, III |
| 5,376,115 A | 12/1994 | Jansen |
| 5,425,759 A | 6/1995 | McDonald |
| 5,476,513 A | 12/1995 | Brady et al. |
| 5,507,805 A | 4/1996 | Koeniger |
| 5,523,029 A | 6/1996 | Korgel et al. |
| 5,562,676 A | 10/1996 | Brady et al. |
| 5,571,177 A | 11/1996 | Deacon et al. |
| 5,578,042 A * | 11/1996 | Cumming .................. 606/107 |
| 5,578,078 A | 11/1996 | Nakajima et al. |
| 5,578,081 A | 11/1996 | McDonald |
| 5,585,049 A | 12/1996 | Grisoni et al. |
| 5,653,754 A | 8/1997 | Nakajima et al. |
| 5,843,187 A | 12/1998 | Bayers |
| 6,152,959 A | 11/2000 | Portney |
| 6,342,058 B1 | 1/2002 | Portney |
| 6,395,028 B1 | 5/2002 | Tran et al. |
| 6,554,860 B2 * | 4/2003 | Hoffmann et al. ......... 623/6.43 |
| 6,562,070 B2 | 5/2003 | Tran et al. |
| 6,755,859 B2 | 6/2004 | Hoffmann et al. |
| 2002/0116062 A1 | 8/2002 | Portney |
| 2003/0018385 A1 | 1/2003 | Tran et al. |

FOREIGN PATENT DOCUMENTS

| | | |
|---|---|---|
| EP | 0 255 759 A1 | 2/1988 |
| EP | 0 766 952 A2 | 4/1997 |
| EP | 0 775 474 B1 | 5/1997 |
| FR | 2 538 697 A1 | 7/1984 |
| FR | 2 749 161 A1 | 12/1997 |
| FR | 2 789 890 A1 | 8/2000 |
| WO | WO 94/18908 A1 | 9/1994 |
| WO | WO-95/21594 A1 | 8/1995 |
| WO | WO 95/32689 A1 | 12/1995 |
| WO | WO 96/07372 A1 | 3/1996 |
| WO | WO 99/62434 A1 | 12/1999 |
| WO | WO 00/78252 A1 | 12/2000 |
| WO | WO-01/87188 A2 | 11/2001 |

* cited by examiner

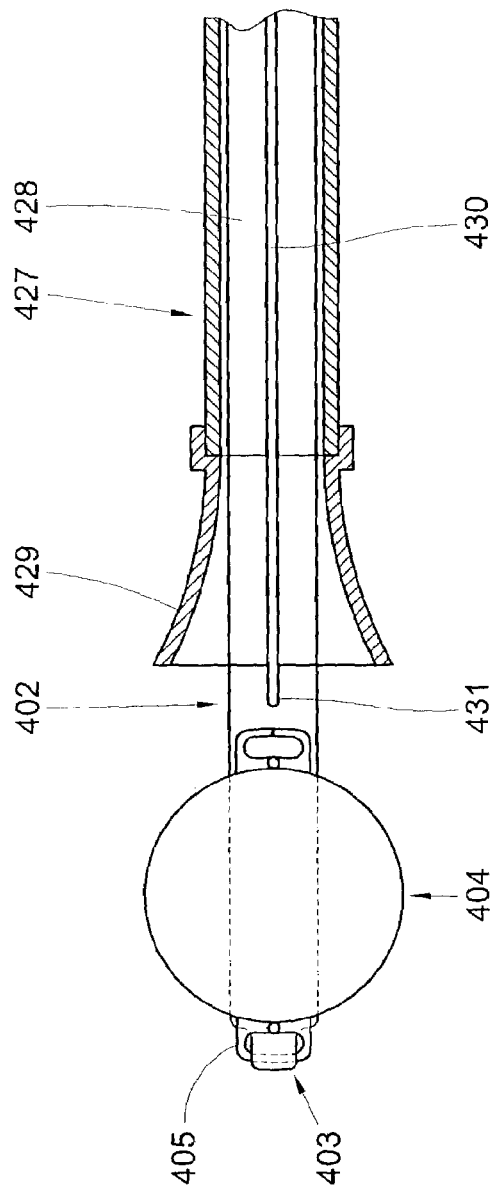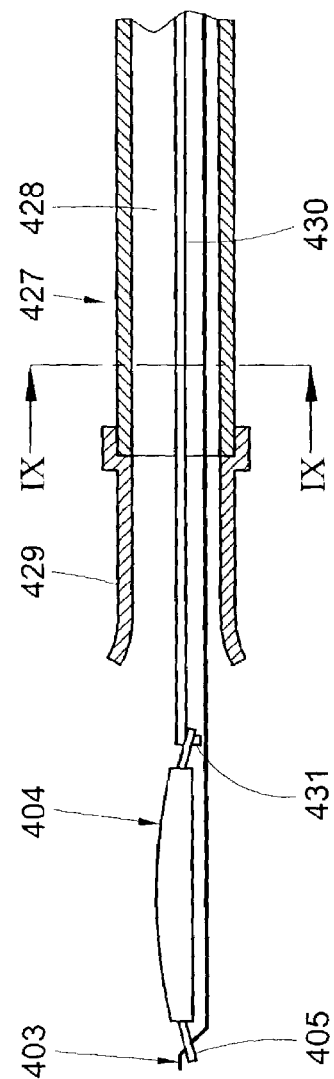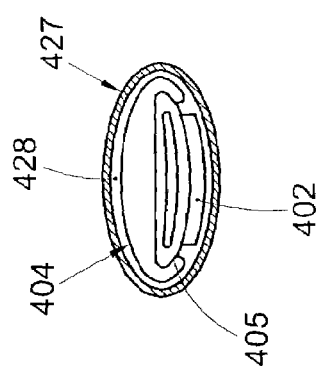

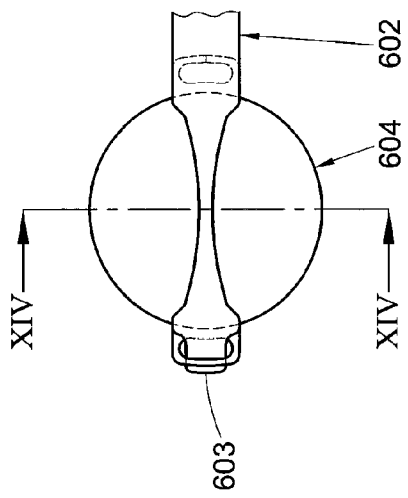
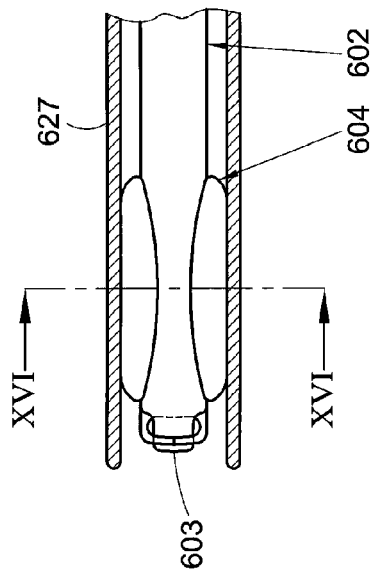
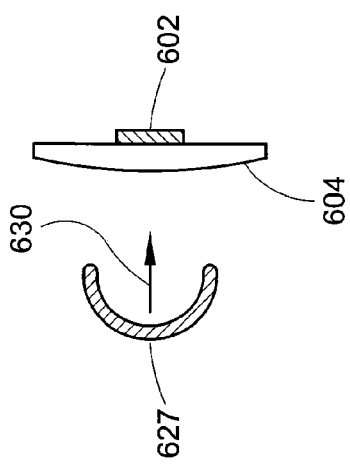
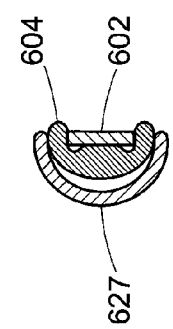
Fig. 15
Fig. 17
Fig. 14
Fig. 16

INTRAOCULAR LENS FOR IMPLANTATION IN AN EYE AND INSTRUMENT AND METHODS FOR INSERTION OF SUCH A LENS

This application claims the benefit of U.S. Provisional Application No. 60/364,514, filed Mar. 15, 2002.

FIELD AND BACKGROUND OF THE INVENTION

The invention relates to a lens, to an instrument for inserting an intraocular lens into an eye, to a method for preparing an intraocular lens for insertion into an eye and to a method for inserting an intraocular lens into an eye, including such a preparatory method. Such a lens, such an instrument and such methods are known from U.S. Pat. No. 4,573,998.

Implantation of an intraocular lens after surgical removal of the opaque lens, a structure having a thickness of about 5 millimeters and diameter of about 9 millimeters, from the eye of a cataract patient is one of the most common forms of eye surgery. The lens is usually implanted in the anterior chamber of the eye (in front of the iris) or in the posterior chamber of the eye (behind the iris) in the capsular bag or in the sulcus.

Another indication for the prescription of intraocular lenses is optical correction of the natural lens. For that purpose the lens is implanted in the anterior chamber of the eye, in front of the natural lens in its natural position. An example of such a lens is disclosed in U.S. Pat. No. 5,192,319. This lens has a rigid optical portion and, disposed along the circumference of the optical portion, haptics in the form of pairs of arms which are flexible but stiff enough to pinch a plea of iris material between free ends thereof for retaining the lens relative to the iris.

The implantation of an intraocular lens involves making a corneal or corneoscleral incision. The intraocular lens is inserted through this incision into the eye. It has long been recognized that it is advantageous if the lens to be implanted can be passed through a small incision, in particular if the natural lens is not removed or if the natural lens is removed after having been emulsified, so that the size of the incision does not have to meet requirements originating from the need to remove the natural lens through that incision. A disadvantage of the rigid intraocular lens is that insertion of the lens requires a relatively large incision in the ocular tissue.

Another option described in this document is to insert the deformable lens via a channel with a circular cross-section. The lens is released from the channel behind the incision. Release of the lens and the position of the lens before insertion in the tube and after release from the tube are difficult to control.

In U.S. Pat. No. 5,047,051, it is proposed to mount the deformable optical portion of the lens to a semi-rigid haptic anchor plate surrounding the deformable optical portion to which anchor plate relatively short looped haptics are attached. However, the semi-rigid anchor plate reduces compressibility of the lens and unfolding of the semi-rigid plate in the anterior chamber of the eye entails a risk of damaging eye tissue bounding the anterior chamber and in particular the cornea.

In U.S. Pat. No. 5,147,395, it is proposed to provide a lens with a fixation member including a deformable element integral with the deformable optic and at least one resilient stiffening element within the deformable element and the optic. This entails that the stiffening element extends within the optic and accordingly reduces the effective optical area of the lens.

In U.S. Pat. No. 5,562,676, it is mentioned to push, pull or carry a lens through a lumen projecting into an eye, for inserting the lens into an eye. For pulling or carrying the lens through the lumen, the use of a forceps is mentioned, which forceps enters the lumen proximally. This entails that the forceps, which needs to extend in the lumen along the lens, occupies a relatively large portion of the cross-section of the lumen in the section of the lumen where the lens is located. Moreover, reliable engagement of the forceps extending through a narrow lumen is difficult to ensure. The lens has relatively slender haptics which can easily be damaged during passage through the lumen.

In international patent application publ. no. WO 95/21594, it is described to suck a lens having a deformable optic into a tube having an internal diameter of 4 mm using a loading funnel. After the distal end of the tube is inserted into the eye, the lens is ejected from the tube by applying pressure to fluid behind the lens. The emergence of the lens from the tube is difficult to control, in particular with respect to the velocity with which the lens regains its original shape and the orientation of the lens after emergence from the tube.

In European patent application 0,766,952 a lens is proposed of which the haptics and the optical part are of shape-recovery materials, the material of the haptics recovering shape more quickly than the material of the lens. Shape recovery is obtained by hydration or temperature. This requires stringent control of the humidity or temperature of the lens before insertion. Furthermore, preparation of the lenses requires hydration or heating, deformation, and drying or cooling in deformed condition, which is relatively cumbersome.

In U.S. Pat. No. 5,843,187, it is described to reduce the transverse dimensions of an intraocular lens during passage through an incision in the eye by stretching the lens in the direction of insertion. To achieve this, holes in the haptics are engaged by micro hooks. Disadvantages of this treatment are that engaging the lens with the micro hooks is cumbersome and that a further incision in the eye is made for insertion of the second micro hook instrument that pulls the lens into the eye. Furthermore, coordinated control of the two instruments inserted into the eye via different incisions is relatively difficult.

SUMMARY OF THE INVENTION

It is an object of the present invention to facilitate control over a lens, which, for inserting the lens into an eye, is passed through a passage, such as an incision or a channel in which the lens is inserted in preparation of insertion into the eye.

According to one aspect of the invention, this object is achieved by providing an intraocular lens comprising an optical portion of a transparent, deformable material, at least one haptic radially projecting from the optical portion for supporting the optical portion in a position parallel to and against an anterior iris surface plane. The at least one haptic has a proximal portion and pair of flexible, pincer like arms projecting from the proximal portion and defining a nip between the arms for pinching and fixating an anterior surface portion of iris tissue. At least one aperture in the at least one haptic is bounded by and located between the pincer-like arms of the at least one haptic. The at least one haptic is of a material having a higher specific stiffness against bending than material of the optical portion, such that flexing of the optical portion in a central zone in-line with said at least one haptic is counteracted. Further, the at least one haptic has a width measured parallel to the plane and perpendicular to the radial direction, which is smaller than the size of the optical portion in the direction of said width, leaving flexibly deformable zones of said optical portion laterally of the central zone. According to another aspect of the invention, this object is achieved by providing an inserting instrument which is specifically adapted for implantation of such a lens. According to yet another aspect of the invention, this object is achieved by providing a method for preparing a lens for insertion into the eye. Such a method can also be combined with further steps to also insert the lens.

The improved control over the orientation of the lens facilitates handling of the lens and immediately after release from the deformed condition in the passage, it reduces the risk of the lens touching sensitive tissue within the eye when released from the passage.

Particular elaborations and embodiments of the invention are set forth in the dependent claims.

Further features, effects and details of the invention appear from the detailed description and the drawings.

BRIEF DESCRIPTION OF THE DRAWINGS

FIG. 7 is a top plan view in cross-section of a distal end portion of a fifth example of an instrument according to the invention and a second example of a lens according to the invention, FIG. 8 is a side view of the arrangement shown in FIG. 7, FIG. 9 is a cross-sectional view along the line IX—IX in FIG. 8 with the lens positioned in a tube portion of the instrument, FIG. 14 is a view in cross-section along the line XIV—XIV in FIG. 15 of a seventh example of an instrument according to the invention and a lens as shown in FIG. 3, FIG. 15 is a bottom view of the arrangement shown in FIG. 14 but excluding a cap shown in FIG. 14, FIG. 16 is a view in cross-section along the line XVI—XVI in FIG. 17, FIG. 17 is a cut-away bottom view of the arrangement shown in FIG. 15, but with the lens engaged by a cap of the instrument.

DETAILED DESCRIPTION

Figure 18:
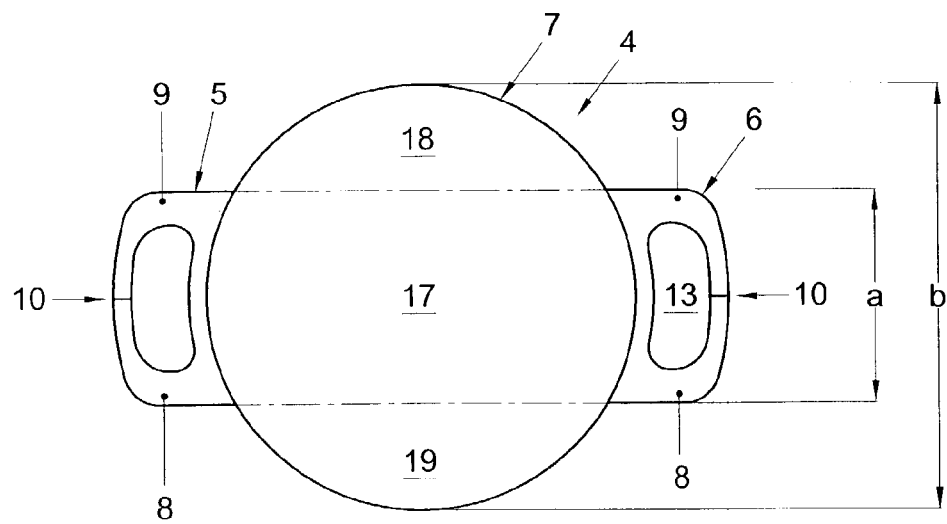
FIG. 18 is a top plan view of the lens shown in FIG. 2.

The invention is first described with reference to FIGS. 1 and 2, in which first examples of an instrument and a lens according to the invention are shown. The lens shown in FIG. 2 is also shown in FIG. 18.

Figure 1:
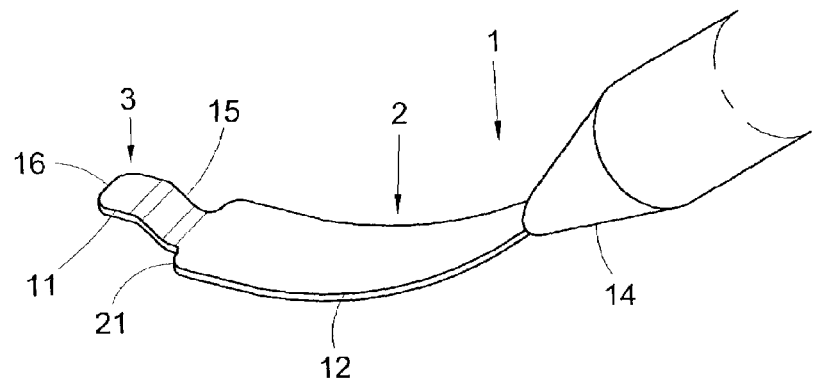
FIG. 1 is a perspective view of a distal portion of a first example of an instrument according to the invention.
Figure 2:
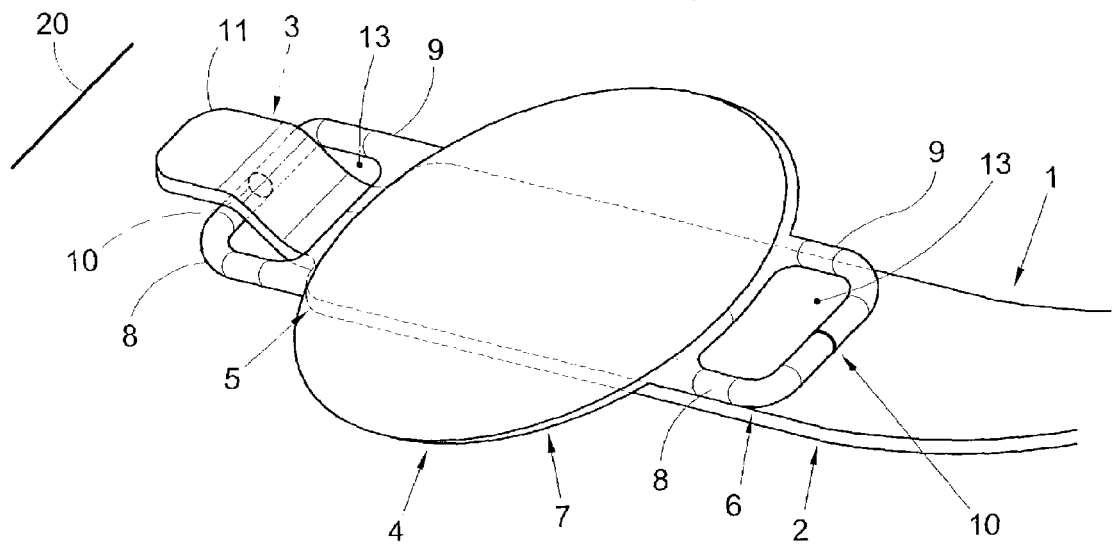
FIG. 2 is an enlarged perspective view of a distal end portion of the instrument according to FIG. 1 and a first example of a lens according to the invention held by the instrument.

The inserting instrument 1 shown in FIGS. 1 and 2 is for inserting an intraocular lens 4 into an eye via an incision 20 (schematically shown in FIG. 2) in the cornea. The instrument 1 has an elongate inserting member 2 projecting from a grip 14 and, at a distal end of the member 2, a hook 3 projecting transversally from the member 2. The lens 4 to be implanted using the instrument 1 has haptics 5, 6 radially projecting from opposite sides of an optical portion 7 of the lens 4. The optical portion 7 is deformable. The haptics 5, 6 are each formed by a pair of arms 8, 9 for clamping iris tissue between surfaces of the arms 8, 9 facing each other in a clamping area 10 and are arranged for supporting the optical portion 7 in a position parallel to and against an anterior iris surface plane when the lens 4 is in implanted condition. In FIG. 2, one of the haptics 5 is located at a side of the optical portion 6 facing the distal end of the inserting member 2 of the instrument I and the other one of the haptics 6 is located at a side of the optical portion 7 facing the proximal end of the inserting member 2 of the instrument 1. The haptics 5, 6 project radially from the optical portion 7 for holding the lens 4 with its optical portion 7 in a position essentially parallel to a plane formed by the anterior surface of the iris when in implanted condition. Apertures 13 are bounded by the haptics 5, 6 and the optical portion 7 is of a transparent, deformable material.

The hook 3 engages the haptic 5 facing the distal end of the inserting member 2. The distal end portion of the inserting member 2 includes wide portions 11, 12 having a width for engaging the lens 4 in laterally spaced apart positions.

In preparation of insertion of the lens 4 into an eye, the lens 4 is positioned with the optical portion 7 against the inserting member 2 and a portion of the haptic 5, which is located distally from the optical portion 7, is engaged by the hook 3. The inserting member 2 then supports the lens engaged by the hook 3.

More specifically, the lens 4 is engaged by the wide portions 11, 12 of the distal end portion in at least laterally spaced apart positions. This counteracts tilting of the lens 4 about the inserting member 2, so that control over the orientation of the lens 4 before and after insertion is improved. This, in turn, is advantageous for facilitating insertion and for avoiding contact between the lens and sensitive tissue in the eye. The support of the lens 4 in laterally spaced apart positions results in the lens being supported in at least three positions, so that its position relative to the inserting member is in principle fully controlled.

The width of the wide portions is preferably at least one millimeter.

According to the present example, the wide portions 11, 12 include a support plateau 12 closely adjacent the hook 3. This support plateau 12 supports the lens 4 engaged by the hook 3. A particular advantage of providing a support plateau, which may have a closed or an open structure, is that lens 4 is easily held in position along the inserting member 2. This effect can be obtained by gravity if the lens 4 is located on top of the inserting member. In addition or alternatively, visco-elastic liquid such as HPMC (Hydroxy PropylMethylCellulose) or Sodiumhyaluron—for instance of the type which is usually injected into the eye to maintain the volume of the anterior chamber--may be applied (preferably liberally) to the lens 4 and/or to the inserting member 2. Such a substance causes the lens 4 to stick to the inserting member 2 and this sticking effect is particularly effective if the substance is located between the relatively large surface formed by the wide portion 12 of the inserting member 2 and the lens 4. The substance also forms a lubricant between the lens 4 and the inserting member 2 reducing friction between the lens 4 and the inserting member 2 if the lens 4 is slid over the inserting member 2 and reducing the risk of damage to the lens 4 and in particular the optical portion 7 of the lens 4.

The wide portion 12 of the inserting member 2 thus defines a plane against which the lens 4 retained closely adjacent the hook 3 such that the inserting instrument reliably supports the lens 4 engaged by the hook 3 prior to insertion of the lens 4 in a well controlled orientation essentially parallel to the wide portion 12. In this example, the width of the wide portion 12 is about two to four millimeters.

During insertion of the lens 4 into the eye, the optical portion 7 of the lens 4 is deformed to a shape which is elongate in the direction of insertion, since the hook 3 pulls the lens 4 through a relatively small incision. After the optical portion 7 has passed the incision 20, it unfolds again and regains its original shape in the anterior chamber of the eye. This allows the optical portion 7 to pass through an incision 20 which is too small for allowing passage of the optical portion 7 in undeformed condition.

After the lens 4 has entered the eye, the wide portion 12 shields the iris and, where applicable, the natural lens from the lens 4 and particularly from the haptics 5, 6, so that the risk of causing damage to these internals of the eye is particularly low.

The hook 3 includes a first section 15 projecting transversely from the inserting member 2 and a second section 16 projecting distally from the first section 15. The second section 16 of the hook 3 includes another one 11 of the wide portions 11, 12. The haptics 5, 6, or at least stiff portions thereof, have a higher stiffness against bending about an axis in longitudinal direction from one haptic 5 to the other haptic 6 than the optical portion 7, at least prior to insertion of the lens. For this purpose, the optical portion of the lens according to this example is made from a material which has a higher specific deformability and a lowe specific stiffness than the material of the haptics 5, 6. Examples of materials for the optical portions are sillicone material and hydrophilic or hydrophobic acrylate. It is generally advantageous if such deformable materials for the optical portion allow an elastic elongation of at least about 50% and more preferably at least about 75%. However, it is also possible to achieve the relatively low stiffness of the optical portion about an axis in longitudinal direction from one haptic to the other haptic by suitably dimensioning the optical portion and the haptics, while the haptics and the optical portion are made of the same material of materials having similar specific stiffness. For instance, the optical portion can be substantially thinner than the dimensions of the haptics in the direction of the optical axis ef the optical portion.

As is best shown in FIG. 18, the relatively inflexible portion has, a width a measured parallel to the support plane defined by the haptics 5, 6 and perpendicular to the longitudinal direction, which is smaller than the width b, measured in the same direction, of the optical portion 7. The stiff portions of the haptics preferably have a width a transverse to the radial direction in which they project smaller than 4 mm and smaller than 80% and more preferably 60% of the width b (measured in the same direction) of the optical portion.

When the lens 4 is engaged by the hook 3, the wide second section 16 of the hook 3 engages the haptic in positions spaced apart transversally to the longitudinal direction of the inserting member 2 and thereby prevents the haptic 5 from tilting about the longitudinal axis of the inserting member 2. Since the haptic 5 is relatively stiff, the forces exerted by the hook 3 onto the haptic 5 are effectively transferred to the deformable optical portion 7 and define a zone 17 longitudinally in-line with the haptic 5 in which flexing of the optical portion 7 is counteracted. Thus, if the optical portion 7 is deformed prior to or during insertion into the eye, the flexural deformation is restrained mainly to lateral zones 18, 19 located laterally of the central zone 17. Thereby, the orientation of the central zone 1 7--and since the haptics 5, 6 and the zone 17 in which the optical portion is least flexed are retained along the inserting member 2 also of the whole lens 4--when the lens regains its original shape is very predictable. The width of the second section 16 of the hook 3 according to this example is 1.5 to 2.5 millimeter.

The second section 16 of the hook 3 is formed by a flat lip. Thus, the end of the inserting member 2 is relatively blunt which reduces the risk of inflicting damage to eye tissue. Moreover, this features facilitates insertion of the hook 3 in the opening 13 bounded by the haptic 5 to be engaged by the hook 3 and the hook 3 can be manufactured easily, for instance by bending plate material or by injection moulding.

The first section 15 of the hook structure 3 extends from a neighboring portion of the inserting member 2 in a direction with a distal component. This allows the hook 3 to be withdrawn easily from the opening 13 in the haptic 5 by simply retracting the inserting member 2 backward in its longitudinal direction, for instance through the insertion 20 after the lens 4 has been inserted in the eye. The angle between the longitudinal direction of the inserting member or at least the portion thereof adjacent the hook 3 and the first portion of the hook 3 projecting therefrom can for instance be at least 200 or at most 700.

According to the present example, the inserting member 2 is a flat strip of plate material. This allows the inserting member 2 to be manufactured in a simple manner and provides sufficient rigidity and flexibility for controlling and maneuvering the lens 4 while occupying very little of the cross-sectional surface of the incision 20 during insertion of the lens 4 into the eye.

As is best seen in FIG. I, a shoulder portion 21 of the inserting member 2 closely adjacent the hook structure 3 has a larger width than the hook structure 3. This prevents the lens 4 engaged by the hook 3 of the inserting member 2 projecting through an opening 13 bounded by the haptic 5 from sliding along the inserting member 2 in the direction of the grip. The shoulder 21 forms an end of a portion of the inserting member 2 having a width larger than the width of the opening 13 and is therefore prevented from passing into the opening 13.

Figure 3:
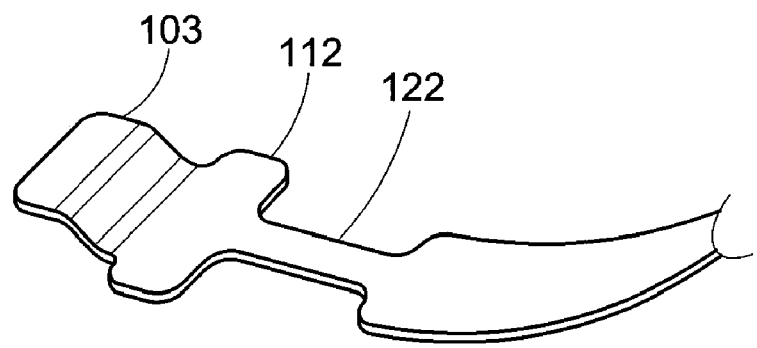
FIG. 3 is a perspective view of a distal end portion of a second example of an instrument according to the invention.

In FIG. 3 an inserting member 102 of an inserting instrument is shown which has a narrow section 122 adjacent the hook structure 103, the narrow section 122 being narrower than the wide portion 112. The narrow section 122 is located where the optical portion of the lens is bent when it is inserted into the eye and interferes less with the bending of the optical portion and occupies less space than if the narrow section is as wide as the wide portion 112 so that room for folded portions of an optical portion of a lens engaged by the inserting member is obtained. This further facilitates passage of the optical portion of the lens through the incision.

Figure 4:
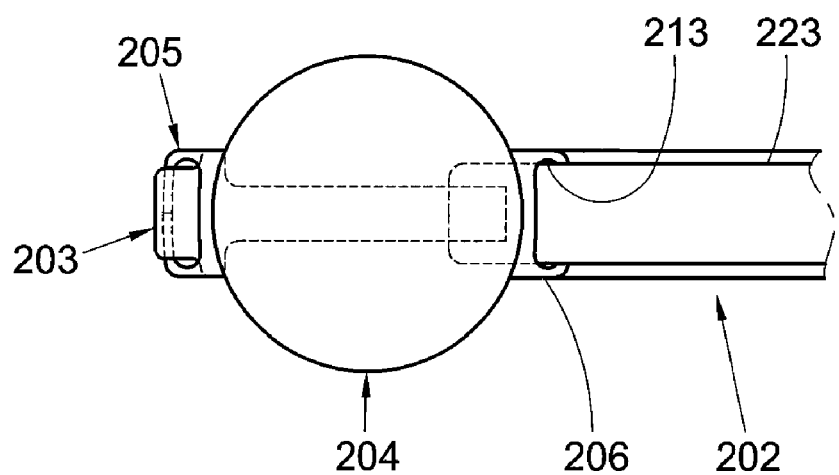
FIG. 4 is a top plan view of a distal end portion of a third example of an instrument according to the invention and a lens as shown in FIG. 2 held by the instrument.
Figure 5:
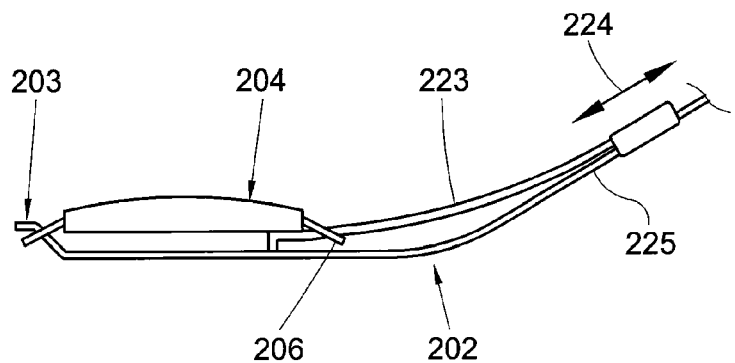
FIG. 5 is a side view of a distal end portion of the instrument and the lens shown in FIG. 4.

As is shown in FIGS. 4 and 5 the inserting instrument may further include an engagement member 223 on a side of the inserting member 202, the engagement member 223 and the hook 203 being located on the same side of the inserting member 202. The engagement member 223 is adapted for engaging a haptic 206 of a lens 204 engaged by the hook 203 and projecting away from the hook 203. Thus, the engagement member 223 can retain the haptic 206 facing away from the hook 203 (and from the haptic 205 engaged thereby) closely to or against the inserting member 202, so that an even more positive control over the lens 204 is obtained. The inserting member 202 according to this example is formed by a flexible strip of metal and can easily be bent away from the engagement member 223. The engagement member 202 can then easily be slipped into the opening 213 in the haptic 206 facing the engagement member 202 by moving the lens 204 in longitudinal direction of the inserting member 202. Engagement between the lens 204 and the hook 203 may have been established beforehand, but may also be established simultaneously or afterwards. When the inserting member 202 is allowed to flex back, the arms of the haptic 206 are retained between the inserting member 202 and the engagement member 233.

To facilitate disengagement of the lens 204 from the engagement member 223 after insertion into the eye, it can be provided that the engagement member 223 can be lifted from the inserting member 202 to release the haptic 206 engaged thereby. To this end, the engagement member 223 can for instance be moveable in longitudinal direction 224 along a portion of the inserting member which extends at an angle to the portion of the engagement member 202 in the area where the haptic 206 is held by the engagement member 223.

Figure 6:
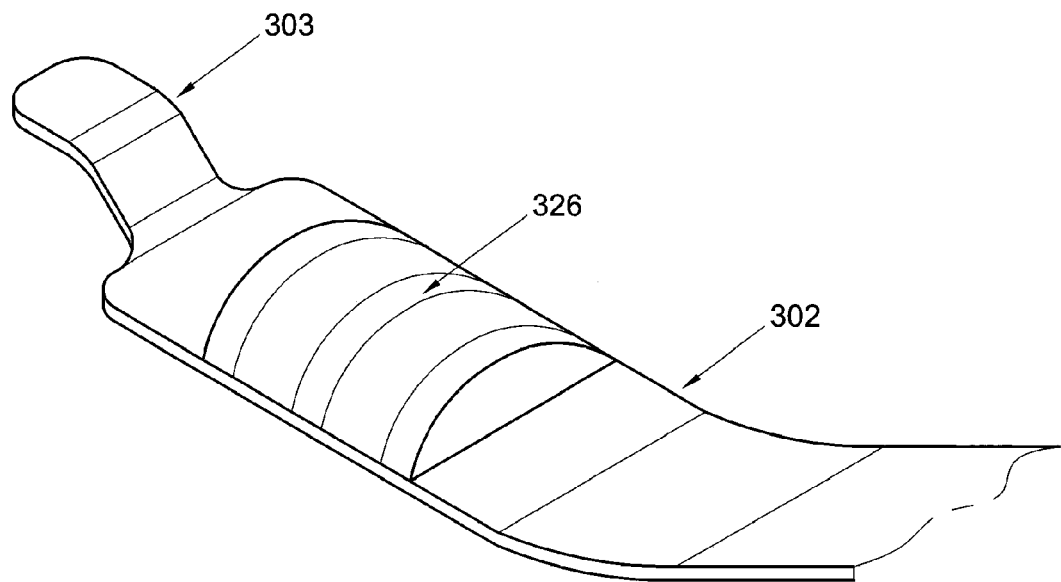
FIG. 6 is a perspective view of a distal end portion of a fourth example of an instrument according to the invention.

In FIG. 6 an inserting member 302 of yet a further example of an inserting instrument according to the invention is shown. According to this example, adjacent the hook structure 303 and at the same side of the inserting member 302 as the hook 303, the inserting member 302 has a section having a projecting central zone 326. The projecting central zone 326 supports flexing of the optical portion of the lens in a predetermined direction with the lateral portions of the optical portion towards the inserting member 302 when the optical portion is forced through a narrow passage, such as the incision in the eye. A similar effect, but in the opposite sense can be achieved by providing that the central portion is recessed. The lateral portions of the optical portion of the lens are then urged to flex away from the inserting member.

In FIGS. 7-9 an embodiment of the invention is shown in which the inserting instrument further includes a feeder tube 427 having a length smaller than the length of the inserting member 402. The feeder tube has an inner channel 428 for receiving a portion of the inserting member 402 and a lens 404 of which the haptic 405 is engaged by the hook 403 and a funnel 429 for compressing the lens 404 during entry into the tube 427. The funnel 429 is removably mourned to a distal end of the tube 427.

In use, the lens 404 is first brought in engagement with the hook 403 of the inserting member 402 projecting from the tube 427 and the funnel 429. Then the lens 404 is pulled into the tube 427, for which purpose for instance suction can be applied to the proximal end of the tube 427 or a pulling shank 430 having a hook 431 at its distal end and a cross-section smaller than the internal cross-section of the feeder tube 427 as shown in FIGS. 7 and 8 can be used. With the lens 404, the inserting member 402 is entrained due the engagement of the hook 403 to the lens 404. The width of the channel 428 of the tube is smaller than the width of the optical portion of the lens 404, so the optical portion has to be deformed during entry into the channel 428 to accommodate to the width of the channel 428. This is facilitated by the funnel 429. After the lens has been pulled into the channel 428, the funnel 429 is removed from the tube 427 to reduce the cross-section of the portion of the instrument to be inserted through the incision in the cornea. Then, the distal end of the tube is inserted into the eye via the incision in the cornea. Next, the inserting member 402 is pushed outward so that the lens is pulled out of the tube 427 and emerges from the distal end of the tube 427 in the eye. Although the use of a tube to maintain deformation of the lens while it is passing through the incision in the cornea entails that part of the effective cross-section of the incision is occupied by the tube, it brings about the advantage, that relatively large forces can be applied to deform the lens and that the forces applied for deforming the lens are not exerted on tissue around the incision in the cornea. It is also possible to hold the tube 427 closely to and in front of the incision through which the lens is to be inserted and to then drive the lens 504 out of the tube and through the incision. 34. After the lens 404 is forced out of a distal end of the tube 427 by the inserting instrument 402, it temporarily remains engaged to the inserting instrument after being released from the tube 427. Accordingly, the lens 404 is engaged to the inserting member 402 at least while it begins to regain its original form, so the position of the lens 404 remains controlled as it is released from the tube and the risk of the lens 404 reaching an undesirable position or uncontrolled touching of internal tissue of the eye by the lens 404 after being released is substantially reduced.

As is best seen in FIG. 9, the tube 427 has an elongate cross-section. This allows an important reduction of the dimensions of the lens 404 transverse to the direction in which the tube extends and in which the lens is to be inserted and the elongate cross-section can be inserted relatively easily through a line-shaped incision.

Figure 11:
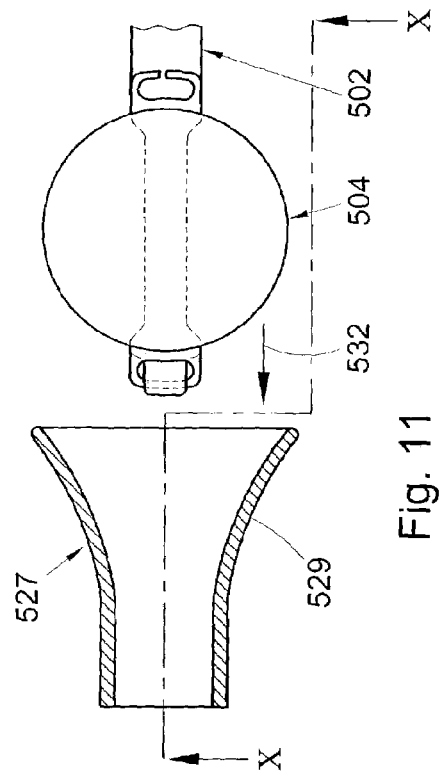
FIG. 11 is a cross-sectional top plan view along the line XI—XI in FIG. 10.
Figure 13:
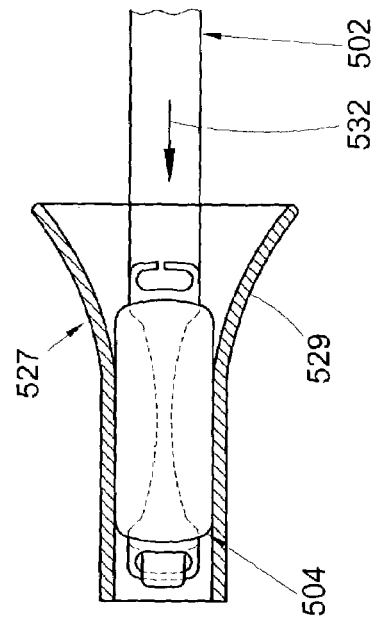
FIG. 13 is a cross-sectional top plan view along the line XIII—XIII in FIG. 12, according to the invention.
Figure 10:
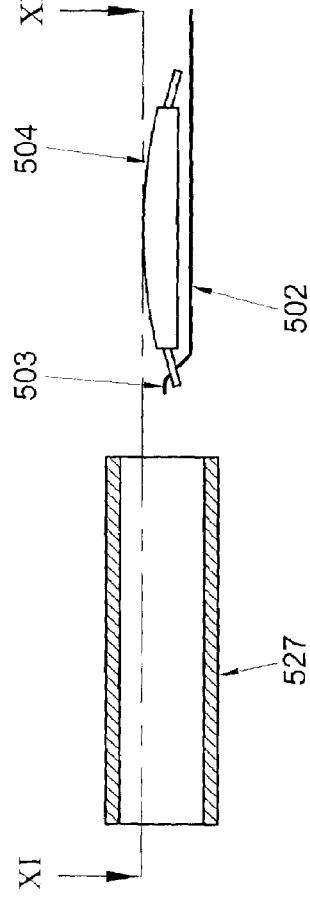
FIG. 10 is a side view in cross-section of a distal end portion of a sixth example of an instrument according to the invention and a lens as shown in FIG. 2 before insertion into, a funnel of the instrument.
Figure 12:
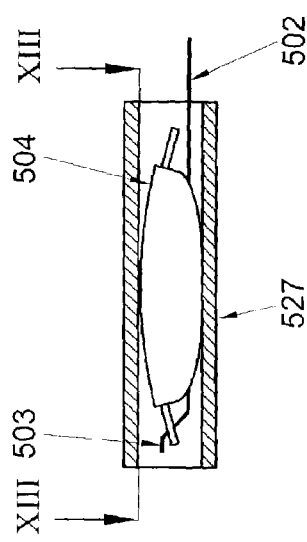
FIG. 12 is a view according to FIG. 10, but with the lens inserted into the funnel.

In FIGS. 10-13 a distal portion of another embodiment of an inserting instrument including a tube 527 in which the lens 504 is inserted is shown. In FIGS. 10 and 11 the lens 504 is shown in a position in font of the funnel 529, in which position it is held by the insertion member 502. The funnel 529 is integrally formed with the tube 527. In FIGS. 12 and 13, the lens 504 is shown after introduction into the tube 527 in the direction of arrow 532 by pushing the inserting member 502 of which the hook 503 engages the lens 504 via the funnel 529 into the narrowest portion of the tube 527. In the condition shown in FIGS. 12 and 13, the lens 504 is ready for insertion. This is accomplished by inserting the end of the tube 527 remote from the funnel 529 into the incision in the cornea of the eye and subsequently pulling the lens 504 out of the distal end of the tube 527 remote from the funnel 529 by moving the inserting member 502 further through the tube 527 in the direction of the arrow 532. Also the tube 527 can be held closely to and in front of the incision through which the lens is to be inserted as the lens 504 is driven out of the tube 527 and through the incision. The lens 504 then unfolds as it passes through the incision.

In FIGS. 14-17 a lens 604 and a distal end portion of an embodiment of an inserting instrument is shown which further includes a cap 627. The cap 627 has a width for receiving a portion of the inserting member 602 adjacent the hook 603 with some play. When the cap 627 is positioned over the inserting member 602 in a direction transverse to the longitudinal direction of the inserting member 602 (arrow 630), lateral portions of the optical portion of the lens 604 engaged by the inserting member 602 are bent around side edges of the inserting member 602. After the cap 627 is positioned over the lens 604 and the inserting member 602, the lens 604 which is held in deformed condition by the cap 627 is inserted into the eye. Next, the cap 627 is pulled back from the eye, thereby releasing the lens 604. Finally, the inserting member is also pulled back from the eye, leaving the lens in the eye for fixation to the iris.

Next, details of the lens shown in FIG. 18 and subsequently of the lenses in FIGS. 19-24 are described and discussed. The dimensions of the apertures 13 of the lens 4 shown in FIG. 18 measured parallel to the plane and perpendicular to the radial direction are larger than the dimensions of the apertures 13 measured in the radial direction. This substantially limits the freedom of rotation of the lens 4 about the first portion 15 of the hook 3, so that the lens 4 engaged by the hook 3 is reliably held in a position essentially aligned with the inserting member 2.

The apertures 13 in the haptics 5, 6 are each bounded by and located between flexible, pincer-like arms 8, 9 of the haptics which arm define a clamping slit 10 between the arms for pinching and fixating an anterior surface portion of iris tissue without penetrating to the posterior surface of the iris. Thus, the apertures 13 between the arms 8, 9 for pinching iris tissue are also used for the purpose of engaging and retaining the lens 4 to the inserting member before and during insertion of the lens 4 into the eye and no separate, additional apertures or constructional elements are required for this purpose.

Figure 19:
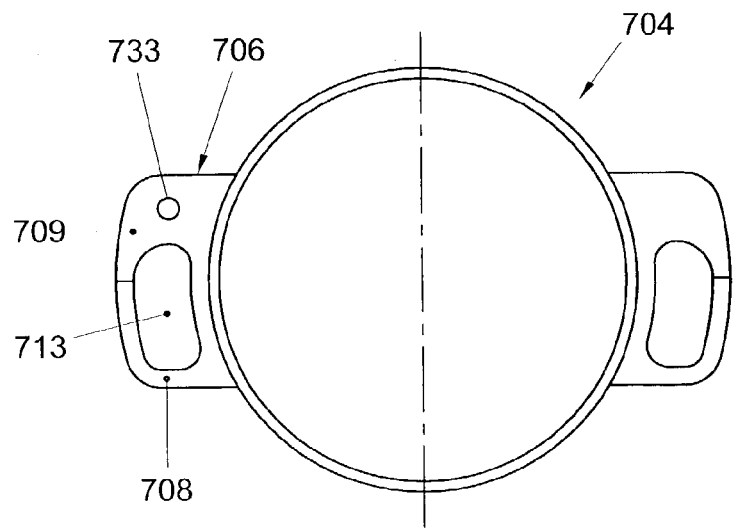
FIG. 19 is a top plan view of a third example of a lens according to the invention.
Figure 20:
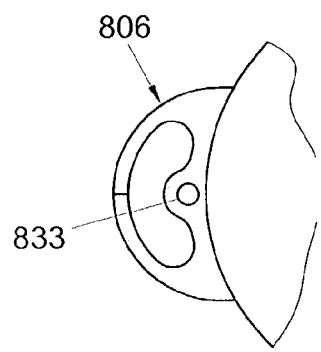
FIG. 20 is a top plan view of a portion including a haptic of a lens as shown in FIG. 7.

In FIG. 19 a lens 704 is shown of which one haptic 706 includes a hole 733 in addition to the aperture 713 between the arms 708, 709. The hole 733 is adapted for engagement by a hook such as the hook 431 and smaller than the aperture 713. Preferably, the hole 733 has a diameter smaller than 1 mm. Another feature of the lens shown in FIG. 19 is that one of the arms 708, 709 is thicker than the other one. This provides room for the additional hole 733. Another advantage of one arm being thicker than the other is, that during the introduction of a plea of iris tissue in the clamping slit between the clamping arms, essentially only the thinner arm flexes so the other arm can be gripped for accurately holding the lens 704 in place. However, a hole 833 for engagement by a hook as the hook 431 can also be provided in a symmetrical haptic 806 as is illustrated by FIG. 20.

Figure 21:
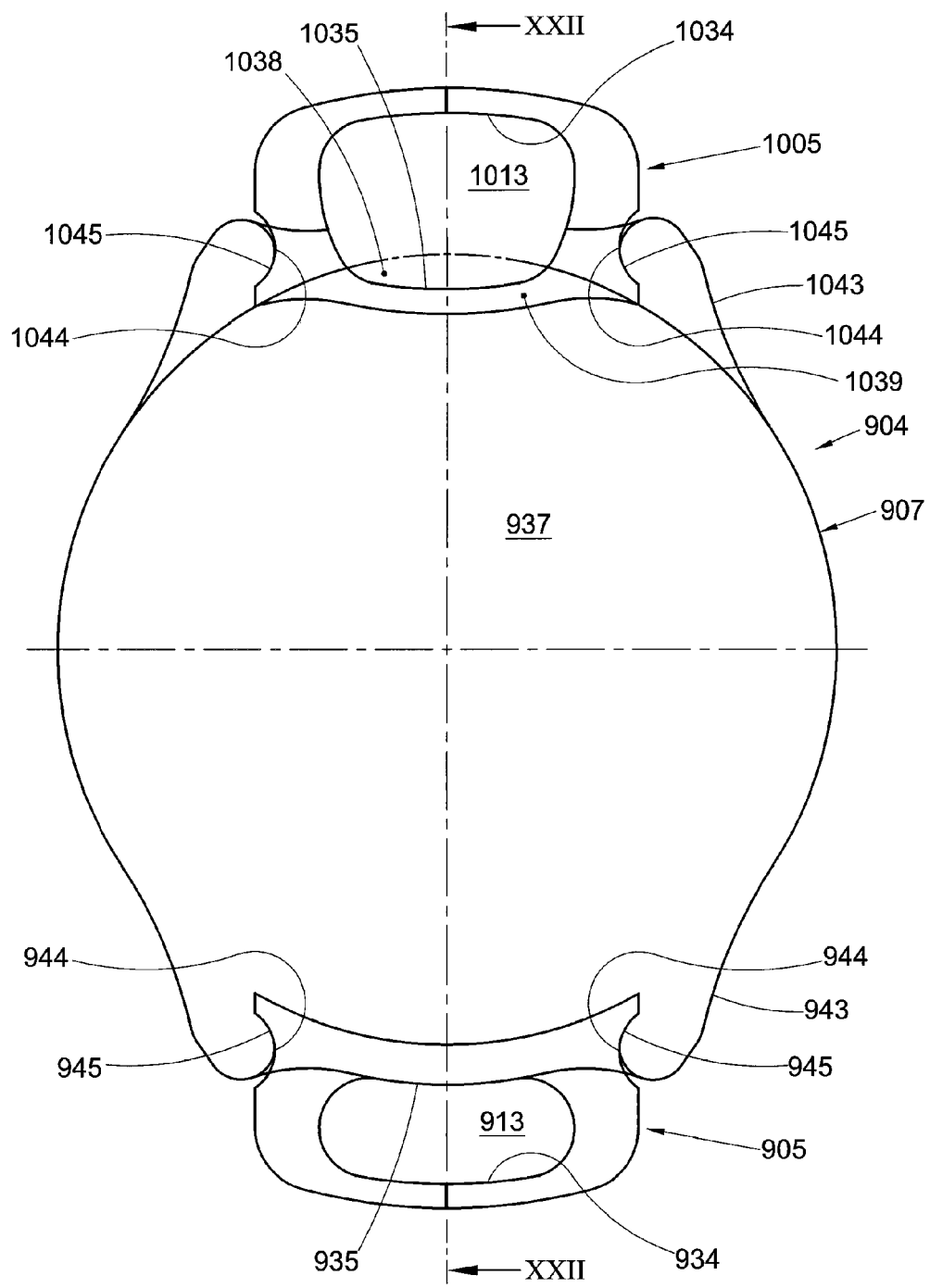
FIG. 21 is a partial top plan view of a fourth and fifth example of a lens according to the invention.
Figure 22:
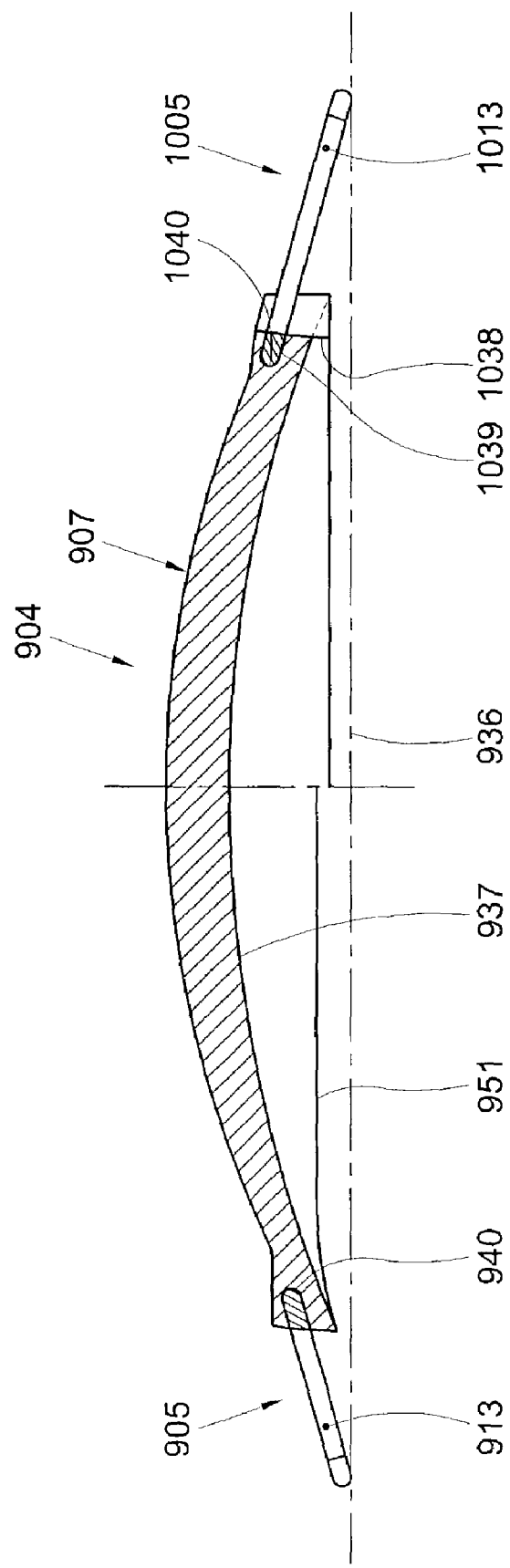
FIG. 22 is a view in cross-section along the line XXII—XXII in FIG. 21.
Figure 23:
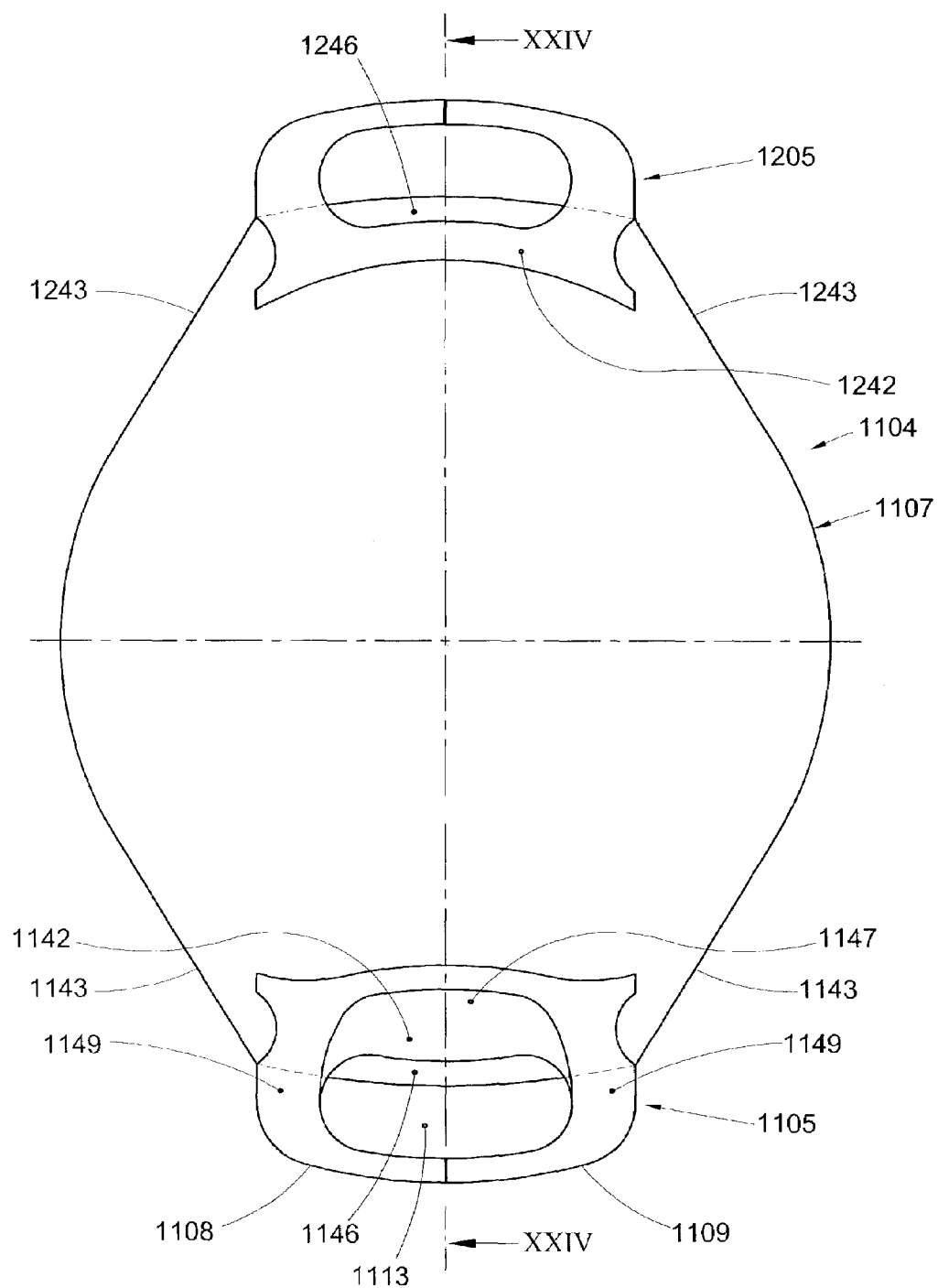
FIG. 23 is a partial top plan view of a sixth and seventh example of a lens according to the invention.
Figure 24:
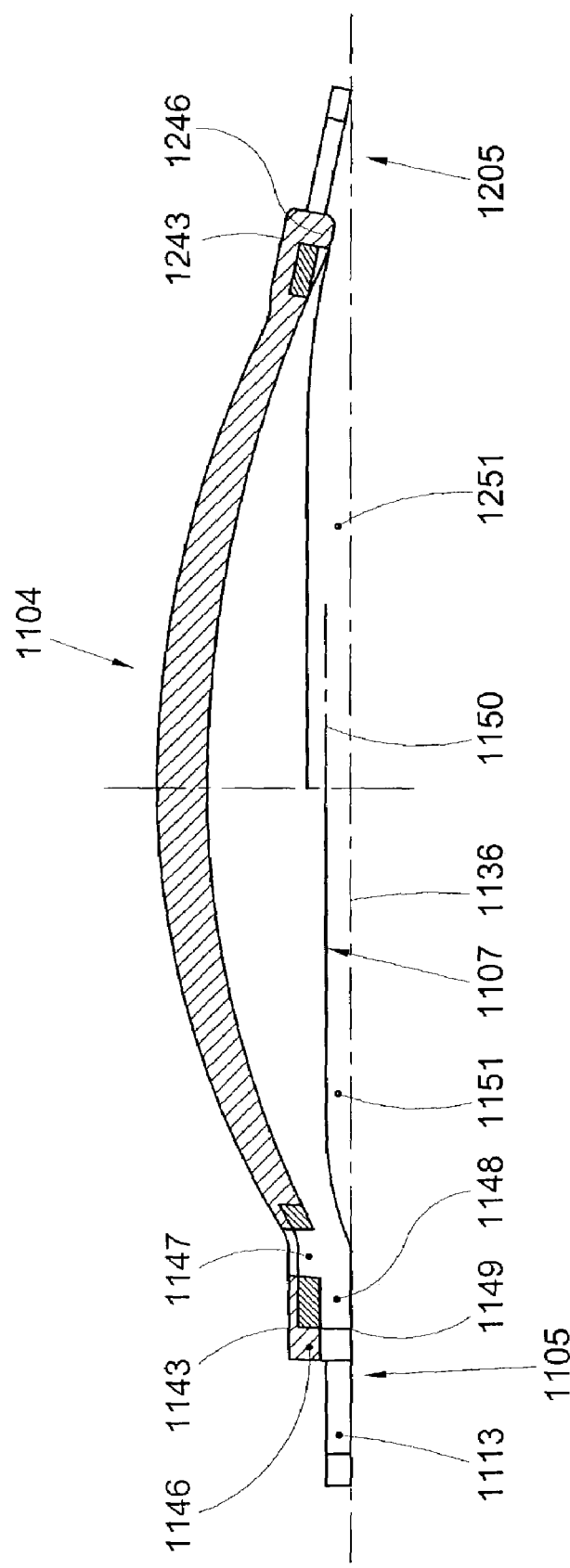
FIG. 24 is a view in cross-section along the line XXIV—XXIV in FIG. 23.

In FIGS. 21 and 22 a lens is shown which, for illustrative purposes, has two different haptics. In practice it is usually preferred to have the same haptics on both sides of the lens. As shown in FIG. 22, the haptics 905, 1005 project posteriorly from the optical portion 907. Of each of the apertures 913, 1013, a portion 934, 1034 most remote from the optical portion 907 is located posteriorly from a portion 935, 1035 nearest to the optical portion 907. This facilitates insertion of the hook 3 and of the engagement member 223 into the apertures, since it allows to insertion thereof in a direction essentially parallel to the plane of the optical portion 907. That the haptics 905, 1005 project posteriorly from the optical portion 907 is also advantageous for keeping the optical portion elevated form the plane defined by the anterior surface of the iris, when in implanted condition. This is advantageous for allowing aqueous flow through the pupil.

The optical portion 907 has a concave posterior surface 937, such that the concave surface 937 bounds a dome-shaped space between the optical portion 907 and the plane 936. One of the haptics 1005 has a lateral side gate 1038 which intersects the concave posterior surface 937 and communicates with the dome-shaped space. Thus, the risk of inhibiting aqueous flow too much is reduced. Even if the posterior peripheral edge of the optical portion 907 is in contact with the iris surface 936, for instance because the haptic 1005 is attached to the iris in the area of a recess in the iris surface, such a lateral side gate 1038 will generally remain open. When such side gates are provided in an optical portion of easily deformable material, as is used for foldable or collapsible lenses, the optical properties in the area adjacent the lateral side gate may easily be affected unfavorably. With a haptic 1005 according to the present example, the likelihood of such effect is reduced, because a portion 1039 of the haptic 1005 extends along the side gate 1038 and stabilizes the optical portion 907 in the area of the lateral side gate 1038.

To achieve a strong bond between the haptic 905, 1005 of a relatively rigid material and the optical portion 907 of a relatively resilient material, while keeping the area occupied by the connection between the haptic 905, 1005 and the optical portion narrow to avoid optical hindrance and to obtain a lens of a compact design, the haptics 905, 1005 are bonded to the optical portion. In this example the bonding is achieved by an adhesive, but direct bonding for instance obtained during injection moulding about an insert. The adhesive is at least partially located in a groove 940, 1040 in the optical portion 907. In addition or alternatively, it is also possible to arrange the adhesive in a groove in the haptic if the haptic and the optical portion are designed accordingly.

To facilitate mounting of the haptics 905, 1005 and to increase the strength of the connection between the haptics 905, 1005 and the optical portion 907, flanges 943, 1043 are provided. The flanges 943 are integrated in the optical portion 907 of which the concave posterior surface 937 extends to the outer ends of the flanges. As can be seen in FIG: 22, this constructional feature results in side gates 951 in the optical portion 907 along the portions of the circumference of the optical portion 907 between the haptics.

The flanges 1043 project from the optical portion 907. The flanges 943, 1043 are provided with bosses 944, 1044 co-operating with recesses 945, 1045 in the haptics. This further reinforces the connection and further provides a snapping action during mounting of the haptics 905, 1005 which facilitates assembly of the lens 904. It is also possible to arrange bosses on the haptics and recesses in the flanges of the optical portion.

Also in F*igs*. 23 and 24 different haptics 1105, 1205 are shown on opposite sides of the lens 1104 for illustrative purposes. Also in this lens, the haptics 1105, 1205 are bonded to the optical portion 1107 by an adhesive. In this lens 1104, the optical portion 1107 and the haptics 1105, 1205 each have a proximal end portion 1142, 1242 enclosed peripherally by positioning portions 1146, 1246 of the flanges 1143, 1243. The adhesive is at least partially located between the haptic 1105, 1205 and the positioning portions 1146, 1246, so that a particularly reliable connection is obtained. The flanges 1143, 1243 are integrated in the optical portion 1107 of which the concave posterior surface extends along posterior surface portions of the flanges. As can be seen in F*ig.* 24, this constructional feature results in side gates 1151, 1251 in the optical portion 1107 along the portions of the circumference of the optical portion 1107 between the haptics. As discussed for other embodiments, the haptics 1105, 1205, or at least stiff portions thereof, have a higher stiffness against bending about an axis in a longitudinal direction from one haptic to the other haptic than the optical portion 1107, at least prior to insertion of the lens. The stiff portions of the haptics preferably have a width transverse to the radial direction in which they project that is smaller than 4 mm.

A particular feature of the haptic 1105 is, that it includes a lateral aperture 1147 in the optical portion 1107 in addition to the aperture 1113 bounded by the clamping arms 1108, 1109. The aperture 1147 in the optical portion 1107 communicates with the dome shaped space bounded by the posterior concave surface of the optical portion 1107. Thus, aqueous flow in the pupillary area is ensured particularly reliably. To further provide passages for aqueous flow in the pupillary area, a lateral port 1148 interconnecting the lateral aperture 1147 in the optical portion 1107 and the aperture 1113 bounded by the clamping arms 1108, 1109. A particularly stable fixation of the lens 1104 to the anterior surface of the iris is obtained, because the haptic 1105 furthermore has support surfaces 1149 defining a plane 1136 essentially parallel to the optical plane 1150 of the optical portion 1107.

Lenses and inserting instruments or members according to the invention are preferably provided in combination as eye treatment kits including an instrument and a lens, the instrument being dimensioned to engage the stiff portion of the lens in the aperture. It is then automatically ensured that the instrument used for implanting the lens fits to the lens.

To further facilitate the implantation, the lens is preferably provided premounted in a position retained by the instrument or at least the inserting member thereof and packaged and sterilized with the instrument or at least the inserting member in a common package. Thus, the need of separately sterilizing the instrument or at least the inserting member is avoided and the risk of contamination of the lens and the inserting member during mounting of the lens to the inserting member is reduced. To reduce waste, used inserting members can be returned to be cleaned, repackaged and sterilized with other lenses to be implanted.

The invention claimed is:

1. An intraocular lens comprising:
an optical portion of a transparent, deformable material;
at least one haptic radially projecting from the optical portion for supporting the optical portion in a position parallel to and against an anterior iris surface plane, said at least one haptic comprising a proximal portion and a pair of flexible, pincer like arms projecting from said proximal portion and defining a nip between said arms for pinching and fixating an anterior surface portion of iris tissue;
at least one aperture in the at least one haptic being bounded by and located between said pincer-like arms of the at least one haptic,
wherein said at least one haptic is of a material having a higher specific stiffness against bending than material of the optical portion, such that flexing of the optical portion in a central zone in-line with said at least one haptic is counteracted, and
wherein said at least one haptic has a width measured parallel to said plane and perpendicular to said radial direction, which is smaller than the size of the optical portion in the direction of said width, leaving flexibly deformable zones of said optical portion laterally of said central zone.

2. A lens according to claim 1, wherein the size of the aperture measured parallel to said plane and perpendicular to said radial direction is larger than the size of the aperture measured in said radial direction.

3. A lens according to claim 1, wherein at least a stiff portion of said at least one haptic has a width transverse to said radial direction smaller than 4 mm.

4. A lens according to claim 1, further comprising a posterior side facing posteriorly towards the iris when in an implanted condition, wherein said at least one haptic projects posteriorly from said optical portion and wherein a portion of said aperture most remote from said optical portion is located posteriorly from a portion of said aperture nearest to said optical portion.

5. A lens according to claim 1, wherein said at least one haptic is bonded to said optical portion.

6. An intraocular lens comprising:
an optical portion of a transparent, deformable material;
at least one haptic radially projecting from the optical portion for supporting the optical portion in a position parallel to and against an anterior iris surface plane, said at least one haptic comprising a proximal portion and a pair of flexible, pincer-like arms projecting from said proximal portion and defining a nip between said arms for pinching and fixating an anterior surface portion of iris tissue, at least one aperture in the at least one haptic being bounded by and located between said pincer-like arms of the at least one haptic,
wherein said at least one haptic is of a material having a higher specific stiffness against bending than material of the optical portion,
wherein said at least one haptic has a width measured parallel to paid plane and perpendicular to said radial direction, which is smaller than the size of the optical portion in the direction of said width,
wherein said at least one haptic is bonded to said optical portion, and
wherein said at least one haptic has a proximal end enclosed peripherally by a positioning portion of at least said optical portion or a flange projecting from said optical portion.

7. A lens according to claim 1, wherein said optical portion has a concave posterior surface such that the concave curve forms a space between said optical portion and said plane, at least one lateral side gate intersecting said concave posterior surface communicating with said space, wherein the material of said at least one haptic extends along said side gate.

8. An eye treatment kit including:
an intraocular lens comprising:
an optical portion of a transparent, deformable material, at least one haptic radially projecting from the optical portion for supporting the optical portion in a position parallel to and against an anterior iris surface plane, said at least one haptic comprising a proximal portion and pair of flexible, pincer-like arms projecting from said proximal portion and defining a nip between said arms for pinching and fixating an anterior surface portion of iris tissue, at least one aperture in the at least one haptic being bounded by and located between said pincer-like arms of the at least one haptic, wherein said at least one haptic is of a material having a higher specific stiffness against bending than the optical portion, such that flexing of the optical portion in a central zone in-line with said at least one haptic is counteracted, and wherein at least said at least one haptic has a width measured parallel to said plane and perpendicular to said radial direction, which is smaller than the size of the optical portion in the direction of said width, leaving flexibly deformable zones of said optical portion laterally of said central portion; and an instrument for inserting the intraocular lens into an eye, comprising an elongate inserting member and, at a distal end of said inserting member, a hook projecting transversally from said inserting member for engaging the at least one haptic of the intraocular lens distally from the optical portion of the lens, wherein said distal end of said inserting member includes a wide portion having a width for engaging said lens in at least laterally spaced apart positions, wherein said hook is adapted to engage said at least one haptic of said lens in said aperture, and includes a first section projecting transversely from a proximally neighboring section of said inserting member and a second section projecting distally from said first section, and wherein said second section of said hook structure includes at least a portion of said wide portion.

9. An eye treatment kit according to claim 8, wherein said lens is retained by said instrument and said lens and said instrument are packaged in a common package.

* * * * *